United States Patent
Kong et al.

(10) Patent No.: US 6,589,752 B1
(45) Date of Patent: Jul. 8, 2003

(54) **RECOMBINANT ANTIGEN OF *TAENIA SOLIUM* METACESTODES**

(76) Inventors: Yoon Kong, Sungkyunkwan University, 300 Chunchun-Dong, Jangan-Ku, Suwon-Si, Kyonggi-Do (KR); Joon-Young Chung, Sungkyunkwan University, 300 Chunchun-Dong, Jangan-Ku, Suwon-Si, Kyonggi-Do (KR); Young Yil Bahk, Sungkyunkwan University, 300 Chunchun-Dong, Jangan-Ku, Suwon-Si, Kyonggi-Do (KR); Shin-Yong Kang, Sungkyunkwan University, 300 Chunchun-Dong, Jangan-Ku, Suwon-Si, Kyonggi-Do (KR); Seung-Yull Cho, Sungkyunkwan University, 300 Chunchun-Dong, Jangan-Ku, Suwon-Si, Kyonggi-Do (KR)

( * ) Notice: Subject to any disclaimer, the term of this patent is extended or adjusted under 35 U.S.C. 154(b) by 39 days.

(21) Appl. No.: 09/676,589

(22) Filed: Sep. 29, 2000

Related U.S. Application Data

(60) Provisional application No. 60/157,388, filed on Oct. 1, 1999.

(51) Int. Cl.[7] .................... G01N 33/53; C12P 21/06; C07H 19/00; C07K 1/00
(52) U.S. Cl. .................. 435/7.22; 435/69.1; 435/7.1; 530/350; 536/23.1
(58) Field of Search ................. 435/7.22, 69.1, 435/7; 530/350, 324; 424/184.1, 191.1, 88; 536/23.1

(56) References Cited

U.S. PATENT DOCUMENTS

| | | | | |
|---|---|---|---|---|
| 5,599,692 A | * | 2/1997 | Harrison et al. | 435/69.3 |
| 5,874,251 A | * | 2/1999 | Zarlenga et al. | 435/69.3 |
| 6,156,505 A | * | 12/2000 | Steinbruch et al. | 435/6 |

OTHER PUBLICATIONS

Chung, J.Y. et al. "A recombinant 10-kDa Protein of *Taenia solium* Metacestodes . . . ", Journal of Infectious Diseases vol. 180, pp 1307–1315, Oct. 1999.*

Gencore Acc# AF076609, Sequence alignment.*

Harrison et al. "Differential diagnosis of *Taenia saginata* and *Taenia solium* with DNA probes" Parasitology, vol. 100, pp. 459–461, 1990.*

(List continued on next page.)

*Primary Examiner*—Lynette R. F. Smith
*Assistant Examiner*—Khatol S Shahnan-Shah
(74) *Attorney, Agent, or Firm*—Albert P. Halluin; Viola T. Kung; Howrey, Simon, Arnold & White, LLP

(57) ABSTRACT

This invention is directed to an isolated DNA sequence encoding an antigen of *Taenia solium* metacestodes. A 10 kDa antigen of *Taenia solium* metacestodes (TSM) has been shown to be specific for immunodiagnosis of Neurocysticercosis (NCC), which is an important cause of neurological disease worldwide. This invention discloses a method of cloning a cDNA library encoding a 10 kDa protein from *Taenia solium* metacestodes. The cloned cDNA contained a 258 bp complete open reading frame, encoding an 86 amino acid protein with a calculated molecular weight of 9,582 Da. It showed 73% homology with a 10 kDa antigen of *T. crassiceps*. The recombinant protein was expressed bacterially as a fusion protein at a high level. A recombinant TSM antigen prepared according: to this invention is useful in detecting neurocysticerocosis disease. In immunoblot with purified recombinant protein, 97% of sera from active NCC showed strong reactivity while 14% of sera from chronic calcified NCC were weekly positive. In 180 sera from patients with other parasitic infections and from normal controls, it revealed 98% specificity.

6 Claims, 8 Drawing Sheets

OTHER PUBLICATIONS

Chapman et al. "Isolation and characterization of species–specific DNA probes from *Taenia solium* and *Taenia saginata* and their use in an egg detection assay", Journal of Clinical Microbiology, vol. 33, No. 5, pp. 1283–1288, May 1995.*

Rishi et al. "Molecular cloning of *Taenia solium* genomic DNA and characterization of taeniid cestodes by DNA analysis" Parasitology, vol. 97 pp. 161–176, 1988.*

Cho, SY, et al., "Biochemical properties of a purified protein in systic fluid of *Taenia Solium* metacestodes," *Korean J. Parasitol.* 24:25–41 (1986).

Fernandez, V, et al. Molecular characterization of a novel 8–kDa subunit of *Echinococcus granulosis* antigen B, *Mol. Biochem. Parasitol.* 77:247–250 (1996).

Gevorkian, G, et al. "Immunodominant synthetic peptides of *Taenia crassiceps* in murine and numan cysticercosis," *Immunol. Lett.* 49:185–189 (1996).

Hayunga EG, et al., "Development of a serological assay for cysticercosis, using an antigen isolated from Taenia spp cyst fluid," *Am. J. Vet. Res.* 52:462–470 (1991).

Tsang VCW, et al., "An enzyme–linked immunoelectrotrasnfer blot assay and glycoprotein antigens for diagnosing human cysticercosis (*Tacnia solium*)," *J. Infect. Dis.* 159:50–59 (1989).

Zarlanga DS, et al., "A *Taenia crassiceps* cDNA sequence encoding a putative immunodiagnostic antigen for bovine cysticercosis," *Mol. Biochem. Parasitol.* 67:215–223 (1994).

* cited by examiner

```
A
-29                                         GAGCCGCACTAACCGAAGTGAAAACAAAG  -1
  1 ATG AGG GCG TCC ATC TTT CTT GCT GTT GCC ATC CTT GTC ATT ACC GTT GTT GCT GCC CCT  60
  1  M   R   A   S   I   F   L   A   V   A   I   L   V   I   T   V   V   A   A   P   20
 61 GAC GAC GAT AAG GGC CAA GAG GAT CTG AAC ATG ACA GTG ATG AAG CAA TTA GGT GAG GTA 120
 21  D   D   D   K   G   Q   E   D   L   N   M   T   V   M   L   Q   L   G   E   V   40
121 CGT CGC TTC TTC ACA GAG GAC CCC CTG GGT AGG AAT GTT ACC AAA CAA CTC AAA GAG ATG 180
 41  R   R   F   F   T   E   D   P   L   G   R   N   V   T   K   Q   L   K   E   M   60
181 ATC GCC ATC GCC AAG GTT ATT AGA CAT CGA ATA AGA AAA TGC CTT GGA GAA TAC TTG AAG 240
 61  I   A   I   A   K   V   I   R   H   R   I   R   K   C   L   G   E   Y   L   K   80
241 GGC CTT GAA AAT GAG TAG AAC TGG CTT AAC CCC ACG AGC CGA AGA GAA TTA ATA AAA GGA TCG 303
 81  G   L   E   N   E   *                                                           86
304 AATTCAACTACA28                                                                    343
```

```
                                                           25
CyDA  M R A S I F L A V A I L V I T V V A A P D D D K G
TclA  M R A S I F L A L A L V I T V A V A P P D D D K G
Eg8   M R T Y I L L S L A V A T V A V V Q A K D E P -

50
CyDA  Q E D L N M T V M L Q L G E V R R F F T E D P L G
TclA  P E D L K K K M M K Q L G E R R F F R E D P L G
Eg8   K A H M G Q V V K R W G E L R D F F R N D P L G

75
CyDA  R N V T K Q L K E M I A K V I P H R I R K C L L
TclA  Q K I D H F Q E T V S I C K A I P E R I R K R L L
Eg8   Q R L V A L G N D L T A I C Q K L Q L K I R E V L

% homology
CyDA  G E Y L K G L - - - - - E N E   *      *
TclA  G E Y L K G L - - - - - E N E   *     86
Eg8   K K Y V K N L V E E K D D D S K         73
                                              33
```

(Highlighted residues: N M T in CyDA row 2; N V T in CyDA row 3)

US 6,589,752 B1

RECOMBINANT ANTIGEN OF *TAENIA SOLIUM* METACESTODES

This application claims the benefit of U.S. Provisional Application No. 60/157,388, filed Oct. 1, 1999.

FIELD OF THE INVENTION

This invention is related to the field of recombinant antigen of *Taenia solium* metacestodes and a method of detecting neurocysticerocosis disease.

BACKGROUND OF THE INVENTION

Neurocysticercosis (NCC), which is caused by infection of the central nervous system with *Taenia solium* metacestodes (TSM), is a major cause of neurological diseases in Asian, African and Latin American people [1, 2, 3]. Surveillance in endemic areas showed that it is of public health concern causing considerable mortality and chronic morbidity as well as economic losses in endemic areas [3, 4]. Substantial evidence has shown that up to 50% of late-onset epilepsy is due to NCC [3–6]. In the United States, over 1,000 cases of NCC are identified each year mostly in immigrants [3, 7].

The diagnosis of NCC can be achieved with a high degree of accuracy by brain computed tomography (CT)/magnetic resonance (MR) [8–10]. These methods are, however, expensive, inaccessible in most endemic areas. Moreover, the number, size and location of the lesions and stage of infection may vary individually. The development of immunological tests, based on the detection of specific antibodies either in sera or in cerebrospinal fluid (CSF), provides a simple and reliable adjuvant for the diagnosis of NCC. Unfortunately, most of the tests employing the crude antigens lack both sensitivity and specificity; cross-reactions occur frequently with other parasitic infections, especially with cystic echinococcosis (CE) and alveolar echinococcosis (AE), which are caused by larval *Echinococcus granulosus* and *E.multilocularis,* respectively [11, 12]. Over the past two decades, many efforts have been directed toward characterizing specific antigens of TSM either from whole worm or from cyst fluid (CF) [11–16]. The low molecular weight antigenic components ranging 8–50 kDa of TSM have attracted particular attention due to their high specificity. In a study with TSM crude soluble extracts by immonoblot, two polypeptides at 8 and 26 kDa were recognized specifically by serum/CSF antibodies of NCC patients or TSM infected pig sera [11, 17] and specific as high as 98% and 100%, respectively. This assay has been widely used for immunodiagnosis of individual patients and for seroepidemiological surveys [4, 18, 19].

Our research interest has been focused on the identification and isolation of specific antigens from CF of TSM. We have previously demonstrated a 10 kDa antigen of TSM CF allowed a high reliability in detecting the specific anti-TSM antibodies in human NCC [12, 15, 16]. Biochemical studies with a monoclonal antibody (mAb) revealed the 10 IcDa antigen is a subunit of a 150 kDa thermostable protein complex [12, 20]. In an experiment to isolate the 10 kDa protein from TSM CF either by mAb-ligand immunoaffinity chromatography [12, 20] or by isoelectric focusing [16], we found that the 10 kDa protein was always linked to other two proteins (15 and 7 kDa, respectively) and could not be separated individually. Nevertheless, immunological evaluation of a fraction containing the three components by both immunoblot and enzyme-linked immunosorbent assay (ELISA) with sera/CSF from NCC and other helminthic infections including AE and CE demonstrated high sensitivity and specificity, both >90% [12, 15, 16].

In the present study, we describe the cloning and sequencing of a cDNA encoding a TSM 10 kDa protein and its expression in *E. coli*. We evaluated its diagnostic value and provided evidence that this recombinant antigen is highly useful in differentiating active NCC from chronic cases and other parasitic infections.

SUMMARY OF THE INVENTION

This invention is directed to an isolated DNA sequence encoding an antigen of *Taenia solium* metacestodes. The DNA sequence is prepared by cloning a cDNA library encoding a 10 kDa protein from *Taenia solium* metacestodes. The DNA sequence comprises the 258-base sequence of the ORF DNA sequence set out in FIG. 2, or its complementary strand, or other DNA sequence which hybridizes to it under stringent conditions. Alternatively, the DNA sequence comprises the 198-base sequence of the truncated fragment of the ORF DNA sequence without the N-terminal hydrophobic sequence, as set out in FIG. 2, or its complementary strand, or other DNA sequence which hybridizes to it under stringent conditions This invention is also directed to a purified recombinant *Taenia solium* metacestodes protein characterized by a molecular weight about 7,000 daltons on SDS-PAGE, wherein said protein is encoded by the 198 bases of the truncated fragment of the ORF DNA sequence without the N-terminal hydrophobic sequence, set out in FIG. 2. This recombinant *Taenia solium* metacestodes protein provides antigencity and can be used in the immunoassay to detect the presence of antibody against *Taenia solium* metacestodes and to diagnose neurocysticercosis diseases. Alternatively, a fusion protein of glutathione S-transferase and the 7,000 kDa *Taenia solium* metacestodes protein can be used as an antigen to detect the presence of antibody against of *Taenia solium* metacestodes in a mammalian subject biological fluid.

BRIEF DESCRIPTION OF FIGURES

FIG. 2. (A) Nucleotide (SEQ ID NO:1) and deduced amino acid sequence (SEQ ID NO:2) of a cDNA encoding the TSM 10 kDs antigen. A complete nucleotide sequence of 372 bp with an ORF of 258 bp is observed. The start (ATG) and stop condons (TAG) are bolded. A putative polyadenylation signal (AATAAA) is underlined. A highly hydrophobic polypeptide sequence is underlined and italicized. Potential N-glycosylation sites are indicated in black box. (B) Alignment of deduced amino acid sequences of the TSM 10 kDa protein (SEQ ID NO:3) with two known taeniid antigens. Gaps indicated by dots are introduced into the sequence to optimize the alignment. Asterisk indicated stop condon. Other markings are same in A. Percent homologies are shown at the end of each polypeptide. Ten kDa immunodiagnostic antigen of *T. crassiceps* [23] (SEQ ID NO:4) and 8 kDs antigen of *E, gratulosus* (subunit of antigen B) [36] (SEQ ID NO:5) are shown for comparison.

DETAILED DESCRIPTION OF INVENTION

Figure 1:
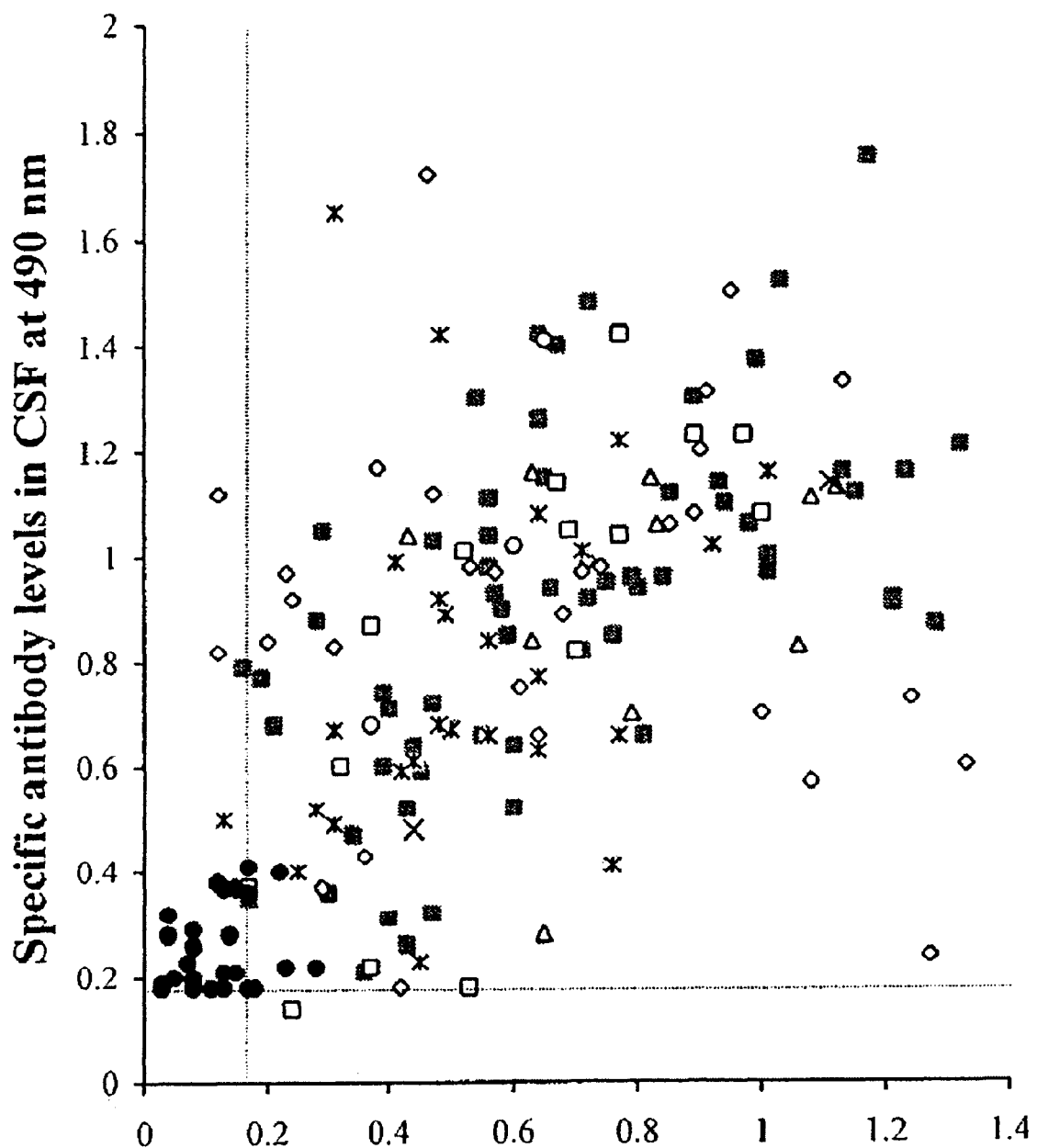
FIG. 1. Specific antibody levels in serum and CSF by ELISA in NCC patients with different neuroimaging findings by CT/MR. The specific antibody levels in patients with chronic inactive NCC were differentiated. Our of 190 active NCC, 152 cases were examined for their specific antibody levels in both sera and CSF. Horizontal and vertical dashed-lines indicate cut-off absorbance (abs.) at 0.18 in both sera and CSF. ■, multiple low-density regions (MLDs); ◇ hydrocephalus, *, MLDs with calcifications; □ cystsic mass (es); △, MLDs with hydrocephalus; O cystic mass with calcification; X, cystic mass with hydrocephalus; and ●, multiple calcifications. The neuroimaging findings of 38 active NCC cases whose sera only tested included multiple low densities (15 cases, abs. between 0.16–1.31), hydrocephalus (10 cases, abs. between 0.32–1.34), cystic mass (5 cases, abs. between 0.27–0.96), MLD mixed with hydrocephalus combined with calcifications (2 cases each, abs. 0.54, 0.64, 0.80 and 0.96, respectively) and spinal cord cysticercosis (1 case, abs. 1.0). These are not plotted in the figure.

This invention is directed to an isolated DNA sequence encoding an antigen of *Taenia solium* metacestodes (TSM). This invention discloses a method of cloning a cDNA encoding TSM 10 kDA protein. Cyst fluid of TSM can be obtained from infected animals, such as pigs. Total RNA are isolated from TSM, and the cDNA library is constructed according to standard procedures. Based on a published cDNA sequence encoding the 10 kDa immunodiagnostic antigen of *T. crassiceps*, degenerate primers are designed and used to perform a reverse transcription polymerase chain reaction (RT-PCR). The PCR product is used as a probe to screen a TSM cDNA library. The phage cDNA is screened by plaque hybridization. The coding region from a cDNA clone is amplified by PCR and expressed in an appropriate host. A preferred method is to express the TSM protein as a fusion protein with glutathione S-transferase (GST) in *E. coli*.

Also encompassed by the invention are polynucleotide sequences that are capable of hybridizing to the claimed nucleotide sequences, and in particular, those shown in FIG. 2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding TSM protein which are encompassed by the invention include deletions, insertions, or substitutions of different nucleotides resulting in a polynucleotide that encodes the same or a functionally equivalent TSM protein. The encoded protein may also contain deletions, insertions, or substitutions of amino acid residues which produce a silent change and result in a functionally equivalent TSM protein. Deliberate amino acid substitutions may be made on the basis of similarity in polarity, charge, solubility, hydrophobicity, hydrophilicity, and/or the amphipathic nature of the residues as long as the biological activity of TSM Protein is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Methods which are well known to those skilled in the art may be used to construct expression vectors containing sequences encoding TSM Protein and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding TSM Protein. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding TSM protein, vectors based on SV40 or EBV may be used with an appropriate selectable marker.

In bacterial systems, a number of expression vectors may be selected depending upon the use intended for TSM. For example, when large quantities of TSM protein are needed for the induction of antibodies, vectors which direct high level expression of fusion proteins that are readily purified may be used. Such vectors include, but are not limited to, the multifunctional *E. coli* cloning and expression vectors such as BLUESCRIPT® (Stratagene), in which the sequence encoding TSM protein may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In this study, we have cloned and sequenced a cDNA encoding TSM 10 kDa protein and expressed it as a GST-fusion protein in *E. coli*. Immunoblot analysis of the recombinant protein employing the patient sera of active and chronic inactive NCC, and other parasitic diseases demonstrated clearly that the recombinant protein has a high potential for serological differentiation of active NCC not only from other parasitic infections but also from chronic inactive NCC.

The effective immunodiagnosis for parasitic diseases depends largely on the availability of well-defined specific antigens. In the case of human and swine cysticercosis as well as bovine cysticercosis (caused by *T. saginata* metacestodes), the difficulties experienced in collecting the metacestodes led researchers to attempt to employ cross-reactive antigenic components from more readily available taemid cestodes as substitute antigens [23, 25–29]. Several studies have demonstrated that the usefulness of a 10 kDa protein in CF of *T. kydatigena* metacestodes for serological diagnosis of human cysticercosis [25] and for bovine cysticercosis [26, 29]. The 10 kDa protein was subsequently found to be shared among metacestodes of *T. saginata* and *T. crassiceps* [23, 25, 30]. This is also true for TSM [12, 15, 16] and confirmed in this study as shown by the comparative immunoblot analysis employing CF antigens of various taeniid metacestodes.

The finding that the 10 kDa antigen of TSM is highly useful for immunodiagnosis of NCC [12, 15, 16] have stimulated our interest in cloning the gene encoding the protein. The common epitope shared between metacestodes of different Taenia species suggests the possibility of exploiting the inherent antigenic similarity of a 10 kDa protein for cloning the corresponding genes. We designed oligonucleotides based on a published cDNA sequence of 10 kDa antigen of *T. crassiceps* and used them as PCR primers to amplify the homologous TSM cDNA, after which we obtained a 270 bp cDNA sequence. By screening a TSM cDNA library with this fragment, we isolated a 372 bp cDNA encoding a 10 kDa protein of TSM.

Sequence analysis revealed that the 372 bp cDNA sequence was closely related to but clearly different from the cDNA sequence encoding 10 kDa antigen of *T. crassiceps* metacestodes. The N-terminus of the deduced protein was shown to contain a highly hydrophobic region which might constitute the transmembrane domain that was possibly finished by signal peptidase [31], or site for hydrophobic interaction with other molecules that had a biological reactivity other than specific antigenicity [25]. Cloning and characterization of the gene encoding the TSM 10 kDa protein may importantly contribute to the further definition of the genetic relationship among 10 kDa proteins shared in different Taenia species.

The major symptoms of active NCC were headache, seizure and symptom complex due to hydrocephalus and IICP while those of chronic cases were seizure and headache. Presumably, persistent inflammatory reactions mounted by active immune surveillance of the host cause several symptoms associated with active NCC [32–34]. The location and size of the worms in the brain that might cause mass effect also affect the clinical manifestations. In chronic NCC, on the other hand, the mummified worms by long standing inflammation served as abnormal epileptogenic focus, stimulating seizures by intensive glyosis, or produced migraine-type headache [8, 10, 24]. Differential diagnosis of active NCC from chronic inactive cases is important to establish the appropriate treatment for the patients since symptoms due to chronic calcified NCC was not caused from the parasites per se but from the sequelae of granuloma and residual calcifications which did not respond anti-cysticercal drug [8, 10]. However, there are few serological methods currently available to assess the worm viability in the patients. CyDA tested in the present study showed high sensitivity and specificity in differentiating active NCC from chronic cases. Expression of a recombinant protein that provides an abundant source of the antigen for immunoblot analysis in a reliable quality has a definitive merit [28].

It is of particular interest to investigate whether CyDA is useful for serological screening of TSM infected pigs. Because *T. solium* splits its life cycle between humans and pigs, the control of porcine cysticercosis is one of the crucial factors for control of human cysticercosis [2, 4, 36]. We are currently analyzing the serum antibody responses of pigs infected with TSM against CyDA. Pilot experiments with several serum samples have shown encouraging results.

CyDA, as characterized in this study, offers effective serological differentiation not only between NCC and other parasitic infections but also between active and chronic inactive NCC. The recombinant 10 kDa TSM protein, 7 KDa TSM protein, or CyDNA can be used for serodiagnosis of TSM infected animals. An immunoassay employing the recombinant TSM antigen can be constructed following standard protocols (Dito, *Diagnostic Medicine*, page 10–18, October 1981 Special Issue; Ullman in *Monoclonal Antibodies and Developments in Immunoassay*, Elsevier/North-Holland Biomedical Press (1981); Wisdom, *Clin. Chem.* 22: 1243–1255 (1976) and U.S. Pat. No. 5,736,344). The immunoassays useful in this invention include ELISAs, radioimmunoassays, fluorescence immunoassay, homogeneous immunoassays, solid-phase immunoassays, etc. The TSM antigen may be labeled with a radioactive molecule, a fluorescent molecule, an enzyme, or a chemiluminescent molecule which serves as a reporter in the assay. An immunocomplex between TSM and the anti-TSM antibody in the biological fluid sample (e.g., blood, urine, saliva, and sweat) from a subject is formed and the presence of the antibody is detected. The invention here may contribute ultimately to the successful control and prevention of NCC.

The examples below are provided to illustrate the subject invention and are not included for the purpose of limiting the invention.

EXAMPLES

Example 1

CF Antigen of Metacestodes from *Taenia solium* and Other Taeniid Cestodes

TSM was obtained from the naturally infected pigs in Korea and China. CF was collected by puncture of intact cysts using sterile syringes, and CF collected [15]. CFs from metacestodes of *T. saginaia, T. taeniaeformis* and *T. crassiceps* were collected from experimentally infected calves, rats and mice, respectively. CFs of *Echinococcus granulosus* and *E. multilocularis* were collected from a CE patient and an experimentally infected rat, respectively. The crude CFs were centrifuged at 20000 g for 1 h and the supernatants were used as CF antigens and stored at −70° C. until use.

Example 2

Cloning of cDNA Encoding of the 10 k Da Protein

Isolation of RNA and construction of cDNA library. Fresh intact TSM were ground in liquid nitrogen. Total RNA was isolated by CsCl gradient ultracentrifugation. Poly(A)+ RNA was prepared by oligo (dT) affinity chromatography (Qiagen, Valencia, Calif.). cDNA was synthesized from 1 μg poly (A)+RNA using Cap-finder cDNA Library Synthesis Kit (Clontech, Palo Alto, Calif.). The resulting cDNA fragments were ligated into EcoRI linker DNA, then digested with EcoRI and finally ligated with EcoRi-cleaved lambda gt 11 phage. The recombinant DNA was packaged in Gigapack III® (gold packaging extract (Stratagene, La Jolla, Calif.). Reverse transcription polymerase chain reaction (RT-PCR) and cloning of cDNA encoding the 10 kDa protein. Based on a published cDNA sequence encoding the 10 kDa immunodiagnostic antigen of *T. crassiceps* (TcA5.5) [23], two oligonucleotide primers were designed and synthesized. The sense primer was 5'-GCGAAAACAAAGATGAGGG-3' (SEQ ID NO:6) and the antisense primer was 5'-CTATTCATTTTCAAGACCC-3' (SEQ ID NO:7). One μg of total RNA was reverse transcribed into cDNA using an oligo d(T)18 primer and Moloney murine leukemia virus reverse transcriptase (Gibco-BRI, Grand islands, N.Y.). The resulting cDNA was subjected to PCR amplification in a 50 μL reaction mixture containing 10 mM Tris-HCl (pH 8.3), 50 mM KCl, 2.5 mM MgC12, 0.2 mM dNTPs, 25 pM each primer and 2.5 units AmpliTaq DNA polymerase (Perkin Elmer, Foster, Calif.). Amplification was carried out in a DNA thermal cycler (Perkin Elmer 9600) for 35 cycles with denaturation at 94° C. for 30 sec, annealing at 56° C. for 30 sec and extension at 72° C. for 30 sec with a final extension at 72° C. for 5 min. The PCR product was analyzed by 1.5% agarose gel electrophoresis. A fragment of 270 bp was isolated and sequenced as described below. The PCR product was finally subcloned into T7 Blue T-vector (Novagen, Madison, Wis.).

Preparing a DNA probe for screening. The antigenic similarity of the 10 kDA protein among genus Taenia demonstrated in previous study [23, 25] suggested a sequence homology of these related genes. We succeeded in using degenerate primers derived from a published cDNA sequence of a 10 kDa immunodiagnostic antigen of *T. crassiceps* (TcA5.5) [23] for amplifying a TSM cDNA. We obtained a 270 bp fragment, of which the deduced amino acid sequence showed significant homology to the 10 kDA of *T. crassiceps*. This fragment was used as a probe to screen a TSM cDNA library, resulting in 30 positive clones.

Screening cDNA library by plaque hybridization. The phage cDNA library was screening by plague hybridization. The labeling of the probe and detection of hybridization signal were performed using the ECL® Direct Nucleic Acid Labelling and Detection System (Amersham, Buckinghamshire, UK). Both prehybridization and hybridization were carried out at 42° C. After secondary wash with high stringency. the membrane was autographed after 1 min exposure. Positive plaques were isolated and the lambda DNA was purified by Qiagen lambda kit (Qiagen). Inserts were closed into pGEM-T easy vector (Promrega, Madison, Wis.) by PCR employing gt 11 universal primer (Promega) and advanced Taq polymerase with proof reading capacity (Contech). Recombinant plasmic in bacterial cultures was purified by Qiagen plasmic midikit (Qiagen).

Screening cDNA library by plaque hybridization. The phage cDNA library was screening by plague hybridization. The labeling of the probe and detection of hybridization signal were, performed using the ECL Direct Nucleic Acid Labelling and Detection System (Amersham, Buckinghamshire, UK). Both prehybridization and hybridization were carried out at 42° C. After secondary wash with high stringency, the membrane was autographed after 1 min exposure. Positive plaques were isolated and the lambda DNA was purified by Qiagen® lambda kit (Qiagen). Inserts were closed into pGEM-T easy vector (Promega, Madison, Wis.) by PCR employing gt 11 universal primer (Promega) and advanced Taq polymerase with proof reading capacity (Contech). Recombinant plasmic in bacterial cultures was purified by Qiagen plasmic midikit (Qiagen).

DNA sequencing and sequence analysis. The nucleotide sequence was determined by dideoxynucleotide chain termination method using the ABI Prisms® Dye Terminator Cycle Sequencing Core Kit (Perkin-Elmer) and an automated DNA sequencer (Applied Biosystems model 373A, Foster City, Calif.). The nucleotide and amino acid sequences were analyzed using the DNA Strider (version 3.0) and the BLAST program of the NCBI databases (Bethesda, Md.).

FIG. 2A shows the nucleotide sequence of the longest insert containing 372 bp (GenBank accession number AF076609). Sequence analysis revealed that a single complete open reading frame (ORF) of 258 bp contained both translation initiation and stop codons, and a poly (A) tail. A putative polyadenylation signal (AATAAA) was identified at 32 bp downstream of the stop codon. Translation of the ORF gave rise to an 86 amino acid polypeptide with a calculated molecular weight of 9582 Da. The N-terminal region was shown to possess a potential hydrophobic domain encompassing residues 4–20. Two putative N-linked glycosylation sites (N-X-S/T) were identified in the middle region. A sequence similarity search revealed that the deduced protein sequence was most closely related to the 10 kDa antigen of *T. crassiceps* by 73% and with 8 kDA subunit of *E. granulosus* antigen B by 33% (FIG. 2B), respectively.

Northern blot analysis using the full-length cDNA as a probe revealed a single RNA transcript of approximately 500 bp in size.

Example 3

Expression and Purification of the Recombinant Protein

The coding region From a cDNA clone was amplified by PCR using a specific primer pair, which contained restriction sites, added to the 5' ends to facilitate cloning of the PCR product. The forward primer was 5'-GTT GGATCCCCTGACGACGATAAG-3' (SEQ ID NO:8) and the reverse primer was 5'-ACTA AAGCTTCTACTCATTTTCAAGG-3 (SEQ ID NO:9, underlined sequences indicated each BamHI and HindII sites). The PCR was carried out as described above and the product was subcloned into pGEM T easy-vector (Promega). An insert isolated from one clone harboring the expected coding sequence was ligated into pGEX 4T-2 expression vector (Pharmacia) and then introduced into E. coli BI.21 cells that carrying the DE3 bacteriophage. The fidelity of the expression construction was confirmed by DNA sequencing. Upon induction with isopropyl-β-D-thiogalactoside (IPTG), the recombinant protein was expressed as a fusion protein with glutathione S-transferase (GST). Induced cells were harvested by centrifugation and lysed by sonication. After clarifying, the supernatant was adsorbed to the glutathione-Sepharose 4B resin (Pharmacia) and the fusion protein was eluted with reduced glutathione. The GST carrier domain in the fusion protein was removed by thrombic cleavage.

Example 4

In vitro Expression and Characterization of a Recombinant Protein

Figure 3:
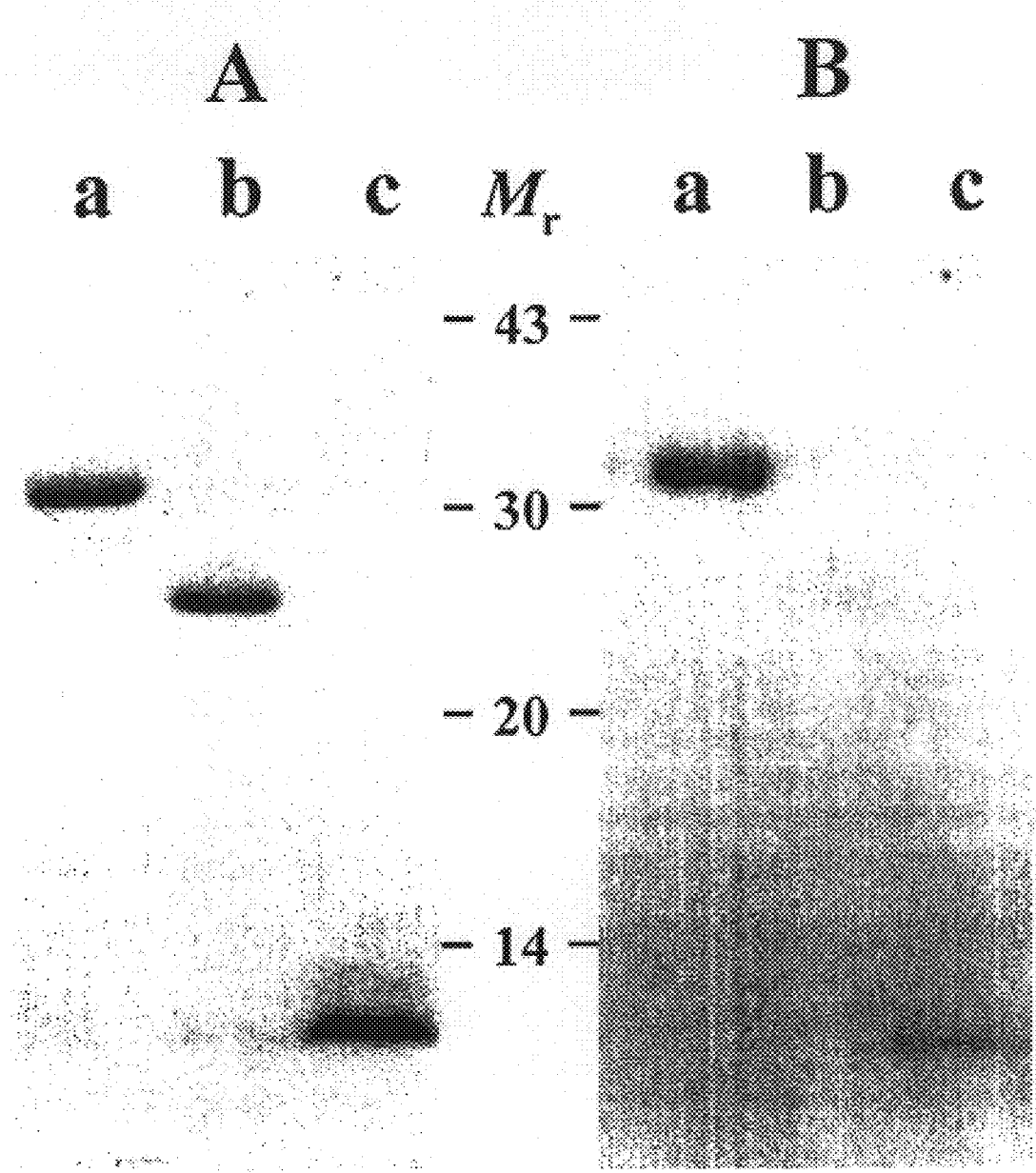
FIG. 3. Analysis of affinity purified recombinant protein by SDS-PAGE stained with Coomassie blue (A) and by immunoblot (B) with a serum pool from 10 NCC patients. Lane a, TSM-GST fusion protein; lane b, TSM fraction after thrombin treatment; lane c, GST protein alone. Mr. Molecular weight in kDa.

In a preliminary experiment, we tried to express the full-length coding domain (258 bp), but only low amount of recombinant protein was expressed as insoluble aggregates. We prepared a truncated fragment of 198 bp without the N-terminal hydrophobic sequence. In this case, the recombinant protein was expressed at a high level in a soluble form and could be efficiently purified by glutathione affinity chromatography. As shown in FIG. 3A, the GST-fusion protein migrated to 33 kDa in SDS-PAGE analysis. After the GST carrier was removed by thrombin cleavage, the purified protein moved as a single band at around 7 kDa, which is in good agreement with that calculated from the cDNA sequence. In immunoblot analysis (FIG. 3B), both the 33 kDa GST-TSM fusion protein and the 7 kDa TSM protein reacted strongly with a pooled serum from 10 NCC patients as well as with the antibodies generated (immunoblots probed by the monospecific antibody and mouse antisera are not shown). On the contrary, no reactivity was observed at the 26 kDa GST band, suggesting that the presence of GST carrier domain in the recombinant protein did not affect the antigenicity (lane b of FIG. 3B). We have designated the 33 kDa recombinant GST-fusion TSM protein as a cysticercosis diagnostic antigen (CyDA) and directly used it in further serological evaluation.

Figure 4:
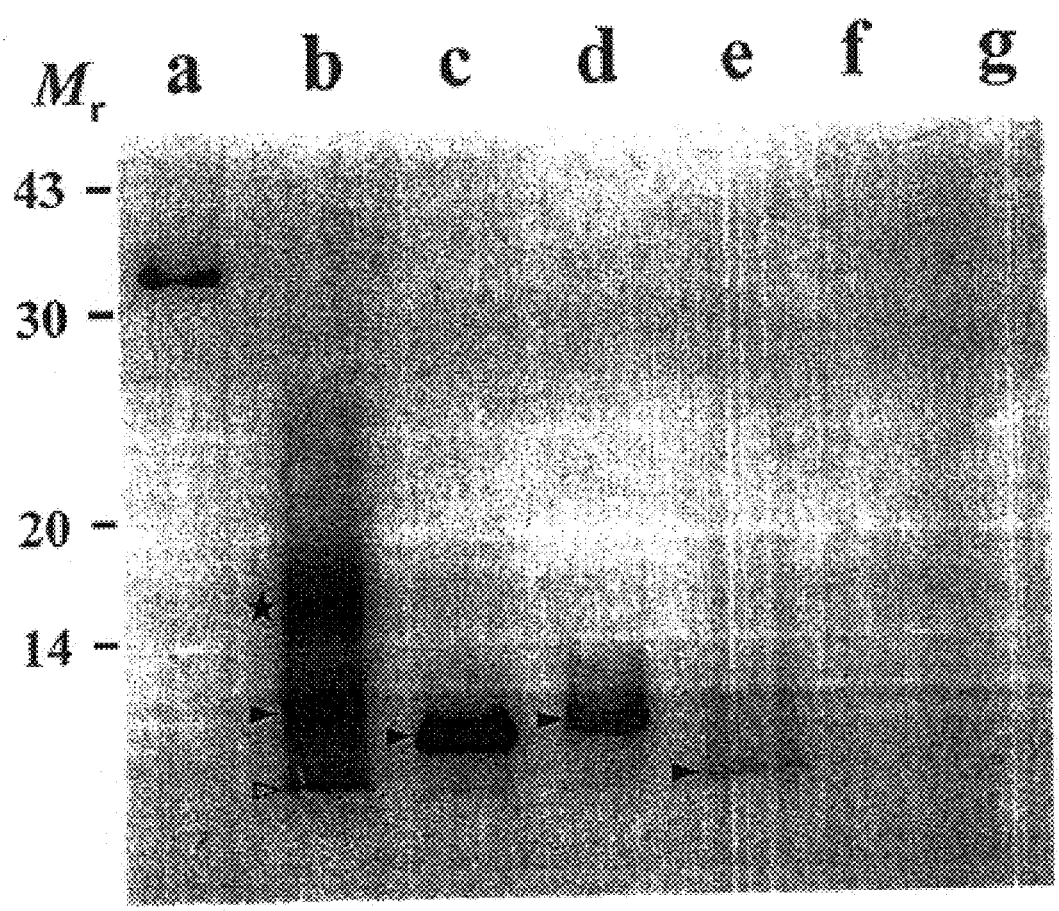
FIG. 4: Immunoblot analysis of CF antigens from different Taenia metacestodes and CyDA against the recombinant the monospecific antibody. A recombinant 33 kDa protein and 10 kDa proteins in Cfs from taetiid metacestodes including TSM show a specific reaction (▶). The 15 kDs (★) and 7 kDa protein (▶) of TSM CF also reveal a positive reaction. Lane b-g. CF antigens from *T. soltum, T. crassicops, T. iaeniaeformis, T. saginata, E. granulosus* and *E. multilocularis*, respectively, M, molecular weights in kDa.

FIG. 4 shows the immunoblot analysis probed with the monospecific antibody purified from NCC patients using CyDA. The proteins at ca. 10 IcDa in CFs from all Taenia species including T. solium, T. saginata, T. crassiceps and T. taeniaeformis were recognized by the monospecific antibody despite a minor difference in the electrophonetic mobility possibly due to their different degree of, or lack of, glycosylation [20, 23 25]. The CF antigens from E. granulosus and E. multilocularis did not show a positive reaction at 10 kDa. This comparative immunoblot analysis confirms the common p[resence of the 10 kDa protein in genus Taenia. Notably, the 15 and 7 kDa bands in CF of TSM were also reactive with the monospecific antibody, further supporting the presumption that the 10 kDa protein is a subunit of the 150 kDa complex of TSM CF [12, 20].

Example 5

Evaluation of the Diagnostic Value of CYDA

Figure 5:
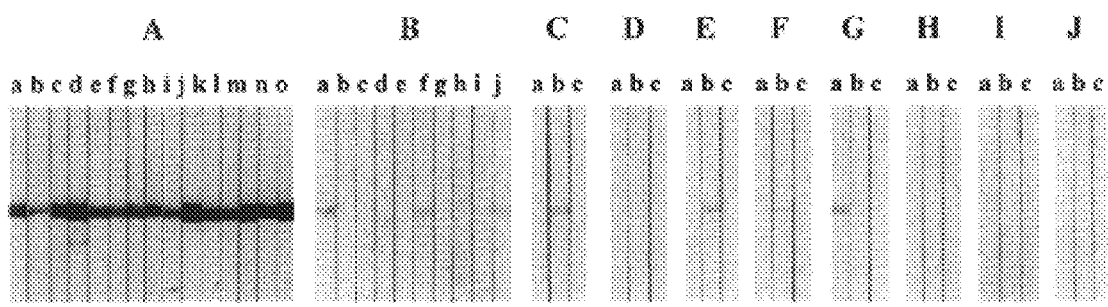
FIG. 5. Immunoblot analysis of CyDA with patient aera from different parasitic infections. Each strip was incubated with an individual serum from patients with active NCC (panel A), chronic calcified NCC (panel B), AE (panel C), CE (panel D), sparganosis (panel E), paragonimiasis (panel F), clonorchiasis (panel G), fascioliasis (panel H), schistosomiasis japonicum (panel 1) and normal controls (panel J). Strong positive reactions are shown only in cases with active NCC. The letters a to o each represent a different patient.
Figure 6:
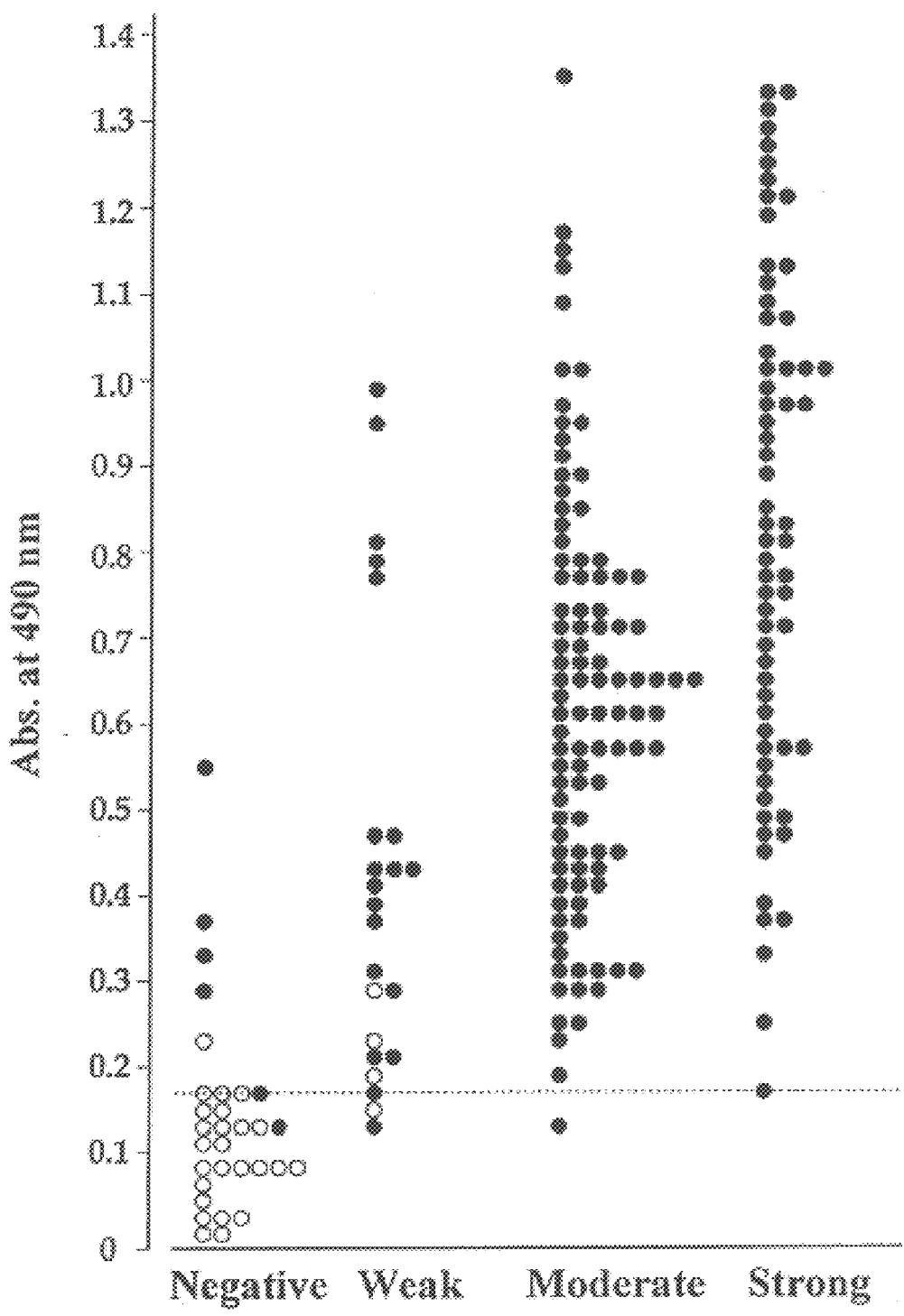
FIG. 6. Correlation between serum antibody activities in immunoblot using CyDA and those in RLISA using crude CF antigen. Horizontal dashed-line indicates the cut-off abs. at 0.18. The typical immunoblot patterns of weak, moderate and strong reactions are shown below the figure. ●, active NCC; O, inactive NCC FIG. 7. Immunoblot analysis of sera of NCC patients.
Figure 7:
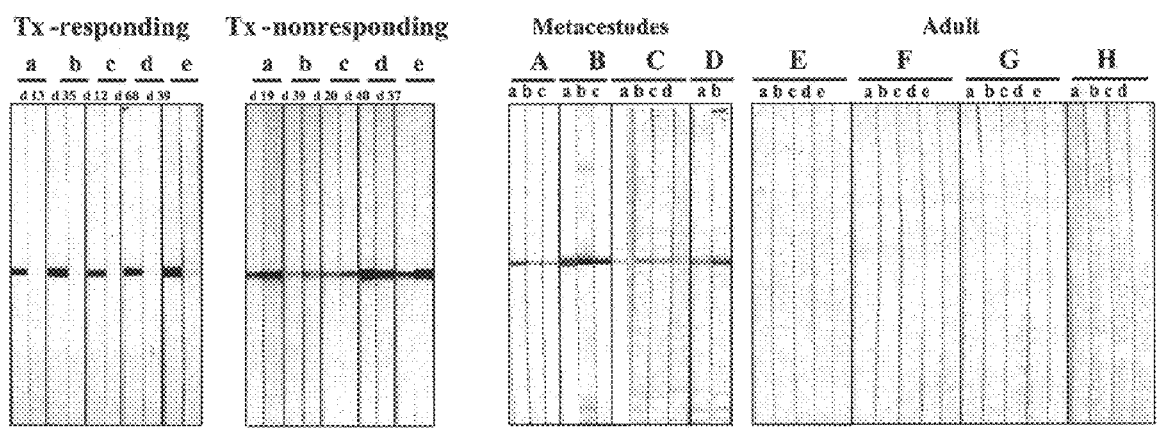

The immunoreactivity of CyDA was further tested by a large-scale immunoblot using individual sera from patients with various helminthic infections to assess the diagnostic value. A typical result of the immunoblot analysis is demonstrated in FIG. 5. A strong recognition of CyDA was observed in 97% (184/190 cases) of sera from patients with active NCC while only 14% (4/29) of sera from chronic NCC showed a weak reaction. Weak cross-reactivity was observed with only a very few of patients with AE, sparganosis or clonarchiasis. None of sera from patients with other parasitic disease or sera from normal controls showed any antibody reactivity. Overall sensitivity and specificity of CyDA were determined to be 97% and 98%, respectively (Table 1). The serum antibody reactivity in NCC patients determined by immunoblot using CyDA appeared to be consistent with those determined by ELISA employing crude CF antigen (FIG. 6).

| Patient category | No. of cases | No. (%) of positive reactions |
| --- | --- | --- |
| Neurocysticercosis | 219 | 188 (88) |
| Active neurocysticercosis | 190 | 184 (97) |
| Chronic neurocysticercosis | 29 | 4 (14) |
| Alveolar echinococcosis | 11 | 1 (9) |
| Cystic echinococcosis | 9 | 9 (0) |
| Sparganosis | 30 | 1 (4) |
| Paragonimiasis | 30 | 0 (0) |
| Clonorchiasis | 30 | 1 (4) |
| Pascioliasis | 10 | 0 (0) |
| Schistosomiasis | 10 | 0 (0) |
| Normal control | 50 | 0 (0) |

Example 6

Preparation of Anti-recombinant TSM Antibodies

Polyclonal antisera against the recombinant TSM protein were produced by immunization of GALB/c mice with purified recombinant TSM protein. A monospecific antibody to the recombinant protein was affinity-purified from a pooled serum from 10 NCC patients using the SulfoLink Kit (Pierce, Rockford, Ill.). Briefly, 10 mg of the recombinant protein was dialyzed against 100 mM sodium acetate buffer, pH 6.0, after which 6 mg of 2-mercaptoethanolamine was added. The mixture was then packed into a column pre-equilibrated with 50 mM Tris buffer, pH 8.5. A total of 5 mL serum was eluted by glycine buffer (100 mM, pH 2.5). The monospecific antibody was dialyzed against 100 mM PBS, pH 7.2 overnight and stored at −70° C. until use.

Example 7

SDS-PAGE and Immunoblot

CF antigen preparations and the recombinant protein were separated by SDS-polyacrylamide gel electrophoresis (PAGE) and transferred to polyvinylidene difluoride (PVDF) membrane (Millipore, Bedford, Mass.). Blots were incubated overnight either with patient sera or with the monospecific antibody diluted at 1:200, respectively. The murine antisera were used in an appropriate dilution. Peroxidase conjugated anti-human IgG (heavy- and light-chain specific, Cappel, West Chester, Pa.) or anti-mouse IgG (whole molecule, Cappel) was diluted at 1:1,000, respectively. The blots were developed with 0.03% (w/v) 4-chloro-1-naphthol (4CIN, Sigma, St. Louis, Mo.).

Example 8

Summary of Patient Characteristics

Serum samples. A total of 219 individual serum samples from NCC patients was selected from our sera bank. Patients were diagnosed by their clinical manifestations and brain CT/MR imaging findings together with positive antibody reactions in the serum/CSF by ELISA with crude TSM CF antigen [9, 21]. Patients were categorized into two groups of 190 active and 29 chronic inactive NCC strictly based on their neuroimaging findings (see Table 2 and FIG. 1). The patients who had lesions with NLD or hydrocephalus compatible with NCC were considered as active cases [8, 10, 21, 22]. On the while, patients who exhibited only multiple calcifications in their CT/MR scan were regarded as chronic inactive cases [8, 10, 22] (see also Table 2 and FIG. 1). In addition, 130 serum samples from cases with AE (11 cases), CE (9 cases), sparganosis (30 cases), paragonimiasis (30 cases), clonorchiasis (30 cases), fascioliasis (10 cases) and schistosomiasis japonicum (10 cases) were used to examine the possible cross-reactivity. Normal controls (50 cases) that denied any possible exposure to helminth infections were also investigated. All serum samples were stored at −70° C. until use.

Table 2 and FIG. 1 show the clinical, serological and radiological profiles of 219 NCC patients enrolled in this study. The 190 cases of active NCC group (123 male and 67 female) had a mean age of 49±15 yrs (9–77 yrs). The common manifestations were headache, seizure and symptoms due to hydrocephalus or increased intracranial pressure (IICP). In addition, some patients presented other neurologic deficits such as dysphasia, hemi- or mono-paresis, dysarthria, paresthesia, stupor or coma and spinal cord syndrome. The majority of this group showed neuroimaging findings of vesicular or colloidal vesicular stage according to Escobar classification [22] and hydrocephalus with/without meningeal irritation sign [8]. They included multiple low densities (MLD), hydrocephalus, cystic mass(es), MLD mixed with calcifications or with hydrocephalus, cystic mass(es) combined with calcifications or with hydrocephalus, and hydrocephalus mixed with calcifications. Spinal cysticercosis together with MLD in CT scan was also observed. Specific anti-TSM antibody levels, determined by ELISA, employing crude CF antigen, were 0.66±0.29 in sera of 190 patients and 0.89±0.38 in CSF of 152 cases examined (other 38 cases were not tested). The cut-off absorbance (abs.) for positive reaction was 0.18 for both serum and CSF [21].

The chronic calcified inactive group consisted of 29 patients whose antibody titers were marginal or negative (0.11±0.07) in serum and positive in CSF (0.25±0.07) (FIG. 1). Chronic NCC tended to show positive reactions only in CSF but not in the sera [14, 21, 24]. These patients included 23 male and 6 female cases. Their mean age was 54±15 yrs (19–83 yrs). Clinical symptoms included seizure, headache and other neurologic deficits such as hemiparesis, dysphasia, motor weakness, dizziness and dementia. All the patients exhibited multiple calcifications in their neuroimage.

TABLE 2

Summary of clinical and neuroimaging profiles of the patients

| Category | Active NCC (n-190) | Inactive NCC (n-29) |
|---|---|---|
| Age (mean (S.D.) | 49 ± 15 | 54 ± 15 |
| Sex (% male) | 65 | 79 |
| Symptoms | | |
| Headache | 122 (64%) | 15 (52%) |
| Seizure | 91 (48%) | 20 (70%) |
| Symptoms due to hydrocephalus[a] | 41 (22%) | 0 |
| Symptoms due to IICP[d] | 31 (16%) | 0 |
| Other neurologic deficits[b] | 41 (22%) | 9 (11%) |
| CT/MR findings | | |
| MLD | 78 (41%) | 0 |
| Hydrocephalus | 41 (22%) | 0 |
| MLD with calcifications | 29 (15%) | 0 |
| Cystic mass(es) | 20 (10%) | 0 |
| MLD with hydrocephalus | 14 (7%) | 0 |
| Cystic mass with calcifications | 3 (2%) | 0 |
| Hydrocephalus with calcifications | 2 (1%) | 0 |
| Cystic mass with hydrocephalus | 2 (1%) | 0 |
| Spinal cord cysticercosis (MLD) | 1 (1%) | 0 |
| Multiple calcifications | 0 | 29 (100%) |

[a]Including nausea, vomiting, gait disturbance, voiding difficulty, memory loss and dizziness presented in patients whose CT/MR revealed hydrocephalus.
[b]Including nausea, vomiting, stiff neck and blurred vision presented in patients whose CT/MR exhibited no evidence of hydrocephalus.
[c]Including dysphasia, hemi- or mono-paresis, dysarthria, paresthesia, stupor, coma and spinal cord symptoms.
[d]Multiple low densities.

Example 9

Follow-up Monitoring of NCC Patient After Treatment

When immunoblot was carried out using individual sera of NCC cases of treatment-responding group (who showed clinical improvement after the therapy), the reactivity against the recombinant protein become weakened or totally disappeared (Tx-responding group). Treatment-nonresponding group, whose symptoms were not relieved with the treatment but remained wax and wane, showed strong positive reactions against the protein in follow-up examination (Tx-nonresponding group). a-e stand for each patient. The time of diagnosis is indicated by d, and numerals indicate the months after the treatment. Panel metacestodes showed the immunoblot analysis with pig sera infected experimentally with *T. solium* eggs (A). The recombinant protein was strongly recognized by pig sera. In addition, the protein was recognized by the sera infected with different Taenia metacestodes (B–D), but not with patient sera infected with adult worms of different Taenia (panel adult, E–H).

REFERENCES

1. Craig P S, Rogan M T, Allan J C. Detection, screening and community epidemiology of taeniid cestode zoonses: Cystic echinococcosis, aleolar echinococcosis and neurocysticercosia. Adv Parasitol 1996;38:170–250.
2. Simanjuntak G M, Margono S S, Okamoto M, Ito A. Taeniasis/cysticercosis in Indonesia as an emerging disease. Parasitol Today 1997;13:321–3.
3. White A C Jr. Neurocysticercosis: A major cause of neurological disease worldwide. Clin Infect Dis 1997;24:101–13.
4. Tsang V C W, Wilson M. *Taenia solium* cysticercosis: An under-recognized but serious public health problem. Parasitol Today 1995;11: 124–6.
5. Medina M T, Rossa E, Rubino-Donnadieu F, Sotelo J. Neurocysticercosis as the main cause of late-onset epilepsy in Mexico. Arch Intern Med 1990;150:323–7.

6. Garcia H H, Gilman R H, Martinez M, et al. Cysticercosis as a major cause of epilepsy in Peru. Lancet 1993;341:197–200.
7. Schantz P M, Moore A C, Munoz I L, et al. Neurocysticercosis in an orthodox Jewish community in New York City. N Eng J Med 1992;327:692–95.
8. Sotelo J, Guerrero V, Rubio F. Neurocysticercosis: A new classification based on active and inactive forms. A study of 753 cases. Arch Intern Med 1985;145:442–45.
9. Chang K H, Kim W S, Cho S Y, Han M C, Kim C W. Comparative evaluation of brain CT and ELISA in the diagnosis of neurocysticercosis. Am J Neuroradiol 1988;9:125–30.
10. Del Brutto O H, Wadia N H, Dumas M, Cruz M, Tsang V C W, Schantz P M. Proposal of diagnostic criteria for human cysticercosis and neurocysticercosis. J Neurol Sci 1996;142:1–6.
11. Gottstein B, Tsang V C W, Schantz P M. Demonstration of species-specific and cross reactive components of *T. solium* metacestode antigens. Am J Trop Med Hyg 1986;35:965–73.
12. Kong Y, Cho S Y, Kim S I, Kang S Y. Immunoelectrophoretic analysis of major component proteins in cystic fluid of *Taenia solium* metacestodes. Korean J Parasitol 1992;30:209–18.
13. Tsang V C W, Brand J A, Boyer A E. An enzyme-linked immunoelectrotransfer blot assay and glycoprotein antigens for diagnosing human cysticercosis (*Tacnia solium*). J Infect Dis 1989;159:50–9.
14. Simac C, Michel P, Andriamsimahavandy A, Esterre P, Michault A. Use of enzyme-linked immunosorbent assay and enzyme-linked immunoelectrotransfer blot for the diagnosis and monitoring of neurocysticercosis. Parasitol Res 1995;81:132–6.
15. Yang H J, Chung J Y, Yun D H, et al. Immunoblot analysis of a 10 kDa amigen in cyst fluid of *Taenia solium* metacestodes. Parasite Immunol 1998;20:483–8.
16. Ito A, Plancarte A, Ma L, et al. Novel antigens for neurocysticercosis: Simple method for preparation and evaluation for serodiagnosis. Am J Trop Med Hyg 1998;59–291–4.
17. Rodriguez-Canul R, Allan J C, Dominguez I L, et al. Application of an immunoassay to determine risk factors associated with porcine cysticercosis in rural areas of Yucatan, Mexico. Vet Parasitol 1998;79:165–80.
18. Wilson M, Bryan R T, Fried J A, et al. Clinical evaluation of the cysticercosis enzyme-linked immunoelectrotransfer blot in patients with neurocysticercosis. J Infect Dis 1991;164:1007–9.
19. Schantz P M, Sarti E, Plancarte A, et al. Community-based epidemiological investigatin of cysticercosis due to *Tanis solium*: Comparison of serological screening tests and clinical fidings in two populations in Mexico. Clin Infect Dis 1994;18:879–85.
20. Cho S Y, Kim S I, Kang S Y, Kong Y. Biochemical properties of a purified protein in cystic fluid of *Taenia solium* metacestodes. Korean J Parasitol 1988;26:87–94.
21. Cho S Y, Kim S I, Kang S Y, et al. Evaluation of enzyme-linked immunosorbent assay in serological diagnosis of human neurocysticercosis using paired samples of serum and cerebrospinal fluid. Korean J Parasitol 1986;24:25–41.
22. Escobar A. The pathology of neurocysticercosis. In: Palacio E. Rodriguez-Cabajal J. Taveras J M, eds. Cysticercosis of the central nervous system. Springfield: Thomas, 1983:27–54.
23. Zarlanga D S, Rhoads M L, Al-Yaman F M. A *Taenia crassieps* cDNA sequence encoding a putative imunodiagnostic antigen for bovine cysticercosis. Mol Biochem parasitol 1994;67:215–23.
24. Del Brutto O H, Sotelo J, Roman G C. eds. Neurocysticercosis: A clinical handbook Lisse: Swets & Zeitlinger Publishers, 1998.
25. Hayunga E G, Sumner M P, Rhoads M L, Murrell K D, Isenstein S P. Development of a serological assay for cysticercosis, using an antigen isolated from Taenia spp cyst fluid. Am J Vet Res 1991p;52:462–70.
26. Kamanga-Sollo E I, Rhoads M L, Murrell K D. Evaluation of an antigenic fraction of *Taenia hydatigena* metacestode cyst fluid for immunodiagnosis of bovine cysticercosis. Am J Vet Res 1987;48:1206–10.
27. Vaz A J, Nunes C M, Piazza R M, et al. Immunoblot with cerebrospinal fluid from patients with neurocysticercosis using antigen from cystioeroi of *Taenia solium* and *Taenia crassiceps*. Am J Trop Med Hyg 1997;57:354–7.
28. Garcia H H, Tsang V C W, Gilman R H. Letter to the editor. Am J Trop Med Hyg 1998;59:693–4.
29. Rhoads M L, Murrell K D, Dilling G W, et al. A potential diagnostic reagent for bovine cysticercosis. J Parasitol 1985;71:779–89.
30. Gevorkian G, Manoutcharian K, Larralde C, et al. Immunodominant synthetic peptides of *Taenia crassiceps* in murine and human cysticercosis. Immunol Lett 1996;49: 185–9.
31. Von Henge G. A new method for predicting signal sequence cleavage site. Nuc Acid Res 1986; 14:4683–90.
32. Ostrosky-Zeichner L, Garcia-Mendoza E, Rios C, Sotelo J. Humoral and cellular immune response within subarachnoid space of patients with neurocysticces. Arch Med Res 1996;27:1–5.
33. Pittella J E H. Neurocysticercosis. Brain Pathol 1997;7:681–93.
34. Evans C A W, Garcia H H, Hartnell A, et al. Elevated concentrations of eotaxin and interleukin-5 in human neurocysticercosis. Infect Immun 1998;66:4522–5.
35. White A C Jr, Robinson P, Kuhn R. *Taenia solium* cysticercosia: Host-parasite interactions and immune response. In: Freedman D O, ed. Immunopathogenetic aspect of diseases induced by halminth parasites. Chemical Immunology. Basel: Karger, 1997;66–209–30.
36. Fernandez V, Ferreira H B, Fernandez C, Zaha A, Nieto A. Molecular characterization of a novel 8-kDa subunit of *Echinococcus granulosis* antigen B. Mol Biochem Parasitol 1996;77:247–50.

What is claimed is:

1. An isolated DNA sequence encoding an antigen of *Taenia solium* metacestodes, said DNA sequence comprising:
   (a) the 258-base sequence of the ORF DNA sequence set out in SEQ ID NO: 1, or its complementary strand; or
   (b) a DNA sequence which hybridizes under stringent conditions to the DNA sequences defined in (a).

2. An isolated DNA sequence encoding an antigen of *Taenia solium* metacestodes, said DNA sequence comprising:
   (a) the 198-base sequence of the truncated fragment of the ORF DNA sequence without the N-terminal hydrophobic sequence, set out in SEQ ID NO: 1, or its complementary strand; or
   (b) a DNA sequence which hybridizes under maximum stringent conditions to the DNA sequences defined in (a).

3. A procaryotic or eucaryotic host cell transformed or transfected with a DNA sequence according to claim 1 or 2, in a manner allowing the host cell to express Taenia solium metacestodes.

4. A biologically functional circular plasmid or viral DNA vector comprising a DNA sequence according to claim 1 or 2.

5. A procaryotic or eucaryotic host cell stably transformed or transfected with a DNA vector according to claim 4.

6. The DNA sequence according to claim 1 or 2, further comprises one or more codons for expression in *E.coli* cells.

* * * * *

SEQUENCE LISTING

<160> NUMBER OF SEQ ID NOS: 9

<210> SEQ ID NO 1
<211> LENGTH: 344
<212> TYPE: DNA
<213> ORGANISM: Taenia solium metacestodes
<220> FEATURE:

-continued

```
<221> NAME/KEY: CDS
<222> LOCATION: (30)...(284)

<400> SEQUENCE: 1
gagccgcact aaccgaagtg aaaacaaag atg agg gcg tcc atc ttt ctt gct       53
                                Met Arg Ala Ser Ile Phe Leu Ala
                                 1               5 gtt gcc atc ctt gtc att acc gtt gtt gct gcc cct gac gac gat aag      101
Val Ala Ile Leu Val Ile Thr Val Val Ala Ala Pro Asp Asp Asp Lys
     10                  15                  20 ggg caa gag gat ctg aac atg aca gtg atg aag caa tta ggt gag gta      149
Gly Gln Glu Asp Leu Asn Met Thr Val Met Lys Gln Leu Gly Glu Val
 25                  30                  35                  40 cgt cgc ttc ttc aca gag gac ccc ctg ggt agg aat gtt acc aaa caa      197
Arg Arg Phe Phe Thr Glu Asp Pro Leu Gly Arg Asn Val Thr Lys Gln
                 45                  50                  55 ctc aaa gag atg atc gcc atc gcc aag gtt att aga cat cga ata aga      245
Leu Lys Glu Met Ile Ala Ile Ala Lys Val Ile Arg His Arg Ile Arg
             60                  65                  70 aaa tgc ctt gga gaa tac ttg aag ggc ctt gaa aat gag tagaactgcg       294
Lys Cys Leu Gly Glu Tyr Leu Lys Gly Leu Glu Asn Glu
         75                  80                  85 cttaacccac gaggcgaaga gaattaataa aaggatcgaa ttcaactaca               344

<210> SEQ ID NO 2
<211> LENGTH: 85
<212> TYPE: PRT
<213> ORGANISM: Taenia solium metacestodes

<400> SEQUENCE: 2

Met Arg Ala Ser Ile Phe Leu Ala Val Ala Ile Leu Val Ile Thr Val
 1               5                  10                  15

Val Ala Ala Pro Asp Asp Asp Lys Gly Gln Glu Asp Leu Asn Met Thr
             20                  25                  30

Val Met Lys Gln Leu Gly Glu Val Arg Arg Phe Phe Thr Glu Asp Pro
         35                  40                  45

Leu Gly Arg Asn Val Thr Lys Gln Leu Lys Glu Met Ile Ala Ile Ala
     50                  55                  60

Lys Val Ile Arg His Arg Ile Arg Lys Cys Leu Gly Glu Tyr Leu Lys
 65                  70                  75                  80

Gly Leu Glu Asn Glu
             85

<210> SEQ ID NO 3
<211> LENGTH: 85
<212> TYPE: PRT
<213> ORGANISM: Taenia solium metacestodes

<400> SEQUENCE: 3

Met Arg Ala Ser Ile Phe Leu Ala Val Ala Ile Leu Val Ile Thr Val
 1               5                  10                  15

Val Ala Ala Pro Asp Asp Asp Lys Gly Gln Glu Asp Leu Asn Met Thr
             20                  25                  30

Val Met Leu Gln Leu Gly Glu Val Arg Arg Phe Phe Thr Glu Asp Pro
         35                  40                  45

Leu Gly Arg Asn Val Thr Lys Gln Leu Lys Glu Met Ile Ala Ile Ala
     50                  55                  60

Lys Val Ile Pro His Arg Ile Arg Lys Cys Leu Gly Glu Tyr Leu Lys
 65                  70                  75                  80
```

Gly Leu Glu Asn Glu
            85

<210> SEQ ID NO 4
<211> LENGTH: 85
<212> TYPE: PRT
<213> ORGANISM: Taenia solium metacestodes

<400> SEQUENCE: 4

Met Arg Ala Ser Thr Phe Leu Ala Leu Ala Ile Leu Val Ile Thr Val
 1               5                  10                  15

Val Ala Ala Pro Pro Asp Asp Lys Gly Pro Glu Asp Leu Lys Lys Lys
            20                  25                  30

Met Met Lys Gln Leu Gly Glu Val Arg Arg Phe Phe Arg Glu Asp Pro
        35                  40                  45

Leu Gly Gln Lys Ile Ile Asp His Phe Gln Glu Thr Val Ser Ile Cys
    50                  55                  60

Lys Ala Ile Pro Glu Arg Ile Arg Lys Arg Leu Gly Glu Tyr Leu Lys
65                  70                  75                  80

Gly Leu Glu Asn Glu
            85

<210> SEQ ID NO 5
<211> LENGTH: 90
<212> TYPE: PRT
<213> ORGANISM: Taenia solium metacestodes

<400> SEQUENCE: 5

Met Arg Thr Tyr Ile Leu Leu Ser Leu Ala Leu Val Ala Thr Val Ala
 1               5                  10                  15

Val Val Gln Ala Lys Asp Glu Pro Lys Ala His Met Gly Gln Val Val
            20                  25                  30

Lys Lys Arg Trp Gly Glu Leu Arg Asp Phe Phe Arg Asn Asp Pro Leu
        35                  40                  45

Gly Gln Arg Leu Val Ala Leu Gly Asn Asp Leu Thr Ala Ile Cys Gln
    50                  55                  60

Lys Leu Gln Leu Lys Ile Arg Glu Val Leu Lys Lys Tyr Val Lys Asn
65                  70                  75                  80

Leu Val Glu Glu Lys Asp Asp Asp Ser Lys
            85                  90

<210> SEQ ID NO 6
<211> LENGTH: 19
<212> TYPE: DNA
<213> ORGANISM: Taenia solium metacestodes

<400> SEQUENCE: 6
gcgaaaacaa agatgaggg                                              19

<210> SEQ ID NO 7
<211> LENGTH: 19
<212> TYPE: DNA
<213> ORGANISM: Taenia solium metacestodes

<400> SEQUENCE: 7
ctattcattt tcaagaccc                                              19

<210> SEQ ID NO 8
<211> LENGTH: 24

```
<212> TYPE: DNA
<213> ORGANISM: Taenia solium metacestodes

<400> SEQUENCE: 8
gttggatccc ctgacgacga taag                                            24

<210> SEQ ID NO 9
<211> LENGTH: 26
<212> TYPE: DNA
<213> ORGANISM: Taenia solium metacestodes

<400> SEQUENCE: 9
actaaagctt ctactcattt tcaagg                                          26
```